(12) United States Patent
Ghurmallah et al.

(10) Patent No.: US 10,131,769 B2
(45) Date of Patent: Nov. 20, 2018

(54) FLAME-RETARDANT POLYSTYENE COMPOSITION

(71) Applicant: SABIC GLOBAL TECHNOLOGIES B.V., Bergen Op Zoom (NL)

(72) Inventors: Ghamdi Ghurmallah, Riyadh (SA); Richard Sott, Borås (SE)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 0 days.

(21) Appl. No.: 15/532,192

(22) PCT Filed: Nov. 30, 2015

(86) PCT No.: PCT/EP2015/078053
§ 371 (c)(1),
(2) Date: Jun. 1, 2017

(87) PCT Pub. No.: WO2016/087365
PCT Pub. Date: Jun. 9, 2016

(65) Prior Publication Data
US 2018/0265676 A1    Sep. 20, 2018

(30) Foreign Application Priority Data
Dec. 5, 2014 (EP) .................................. 14196434

(51) Int. Cl.
| | | |
|---|---|---|
| *C08K 5/53* | (2006.01) |
| *C08L 25/06* | (2006.01) |
| *C08K 5/5399* | (2006.01) |
| *C07F 9/572* | (2006.01) |
| *C08L 71/12* | (2006.01) |

(52) U.S. Cl.
CPC .......... *C08K 5/5399* (2013.01); *C07F 9/5721* (2013.01); *C08L 25/06* (2013.01); *C08L 71/123* (2013.01); *C08L 2201/02* (2013.01)

(58) Field of Classification Search
CPC ... C08K 5/5399; C07F 9/5721; C08L 71/123; C08L 25/06; C08L 2201/02
USPC .......................................................... 524/104
See application file for complete search history.

(56) References Cited

U.S. PATENT DOCUMENTS

| | | |
|---|---|---|
| 3,078,254 A | 2/1963 | Zelinsk |
| 3,257,357 A | 6/1966 | Stamatoff |
| 3,257,358 A | 6/1966 | Stamatoff |
| 3,265,765 A | 8/1966 | Holden |
| 3,297,793 A | 1/1967 | Dollinger |
| 3,306,874 A | 2/1967 | Hay |
| 3,306,875 A | 2/1967 | Hay |
| 3,402,159 A | 9/1968 | Hsieh |
| 3,594,452 A | 7/1971 | De La Mare |
| 3,937,765 A * | 2/1976 | Toy .................... C07F 9/242 428/921 |
| 2004/0249029 A1 | 12/2004 | Iwaki et al. |
| 2012/0178842 A1 | 7/2012 | Hahn et al. |
| 2014/0128489 A1 | 5/2014 | Eberstaller et al. |

FOREIGN PATENT DOCUMENTS

| | | |
|---|---|---|
| GB | 1264741 | 2/1972 |
| JP | 2000154277 A * | 6/2000 |
| JP | 2000154277 A | 6/2000 |
| WO | 2013034276 A1 | 3/2013 |

OTHER PUBLICATIONS

International Search Report and the Written Opinion of the International Searching Authority for PCT/EP2015/078053 dated Feb. 11, 2016, 11 pages.

* cited by examiner

*Primary Examiner* — Michael Bernshteyn
(74) *Attorney, Agent, or Firm* — Cantor Colburn LLP

(57) ABSTRACT

The invention relates to a polystyrene composition comprising a polystyrene and compound according to formula (III).

6 Claims, 1 Drawing Sheet

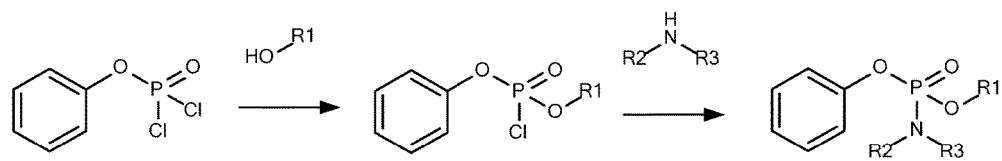

FLAME-RETARDANT POLYSTYENE COMPOSITION

This application is a national stage application of PCT/EP2015/078053, filed Nov. 30, 2015, which claims priority to European Patent Application 14196434.6 filed Dec. 5, 2014, both of which are hereby incorporated by reference in their entirety.

The invention relates to a halogen free flame-retardant polystyrene composition, to a halogen free flame-retardant compound and to the use of such flame-retardant compound.

The addition of flame retardants to polymer compositions is important and/or mandatory in many fields. Regulations on the use of polystyrene particle foams made of expandable polystyrene (EPS) or regulations on the use of polystyrene extrusion foam plates (XPS) as heat-insulating material for buildings require flame-retardancy in most cases. Polystyrene homo- and copolymers are predominantly rendered flame-resistant using halogen-containing, particularly brominated, organic compounds such as hexabromocyclo-dodecane (HBCD). However, this compound and a number of other brominated substances have been subjected to debate and/or were already banned due to the potential environmental and health hazard of these compounds.

As an alternative, halogen-free flame retardants for EPS have been explored. However, halogen-free flame retardants need to be used in substantially higher amounts for achieving the same flame-retardant effect as the halogen-containing flame retardants.

It is partly for this reason that halogen-free flame retardants, which are employed in solid polymers, cannot be used in the same manner in polymeric foams. Halogen-free flame retardants can interfere with the foaming process or can affect the mechanical and thermal properties of the polymeric foam. Moreover, in preparing expandable polystyrene by suspension polymerization, the high amounts of flame retardant may reduce stability of the suspension and can thus interfere with and/or affect the preparation process.

The effect of the flame retardants used in solid polymers is often unpredictable in polymeric foams, due to the particularities of such foams and due to differing fire tests.

As an example of halogen-free flame retardants, US2012/0178842 describes a process for the production of EPS rendered flame-retardant by a halogen-free method. In this method, acylcic oligophosphine chalcogenides having from 2 to 6 phosphorus atoms and having at least one phosphorus-phosphorus bond are used as a flame retardant.

US2014/0128489 describes flame-retardant expandable polymers. The flame-retardant properties are provided by specific phosphorous compounds such as 10-hydroxy-9,10-dihydro-9-oxa-10-phosphaphenanthrene-10-oxide.

There is still a need for a halogen-free flame retardant for expandable polystyrene that works at concentrations suitable for EPS preparation.

It is an aim of the present invention to provide a sufficiently fire-resistant, flame-retardant, expandable polystyrene composition. It is a further objective of the invention to provide such polystyrene composition with good foamability and good mechanical stability.

Accordingly, the present invention provides a polystyrene composition comprising a polystyrene and a compound according to formula (I),

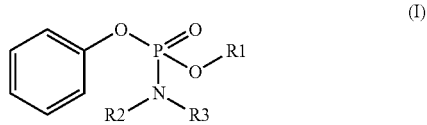

(I)

wherein R1 is a substituted or an unsubstituted aryl group comprising 6-30 carbon atoms and R2 and R3 are independently chosen from the group consisting of hydrogen and alkyl groups, cycloalkyl groups, aryl groups, allyl groups and aralkyl groups comprising 1-20 carbon atoms, or form a ring together with the nitrogen atom attached to the phosphorous atom.

The polystyrene composition according to the invention has a good flame retardancy.

Preferably, the amount of the compound (I) (such as (III) as mentioned later) is 1-10 wt % of the total composition.

Preferably, in formula (I), R1 is a substituted or an unsubstituted phenyl group. More preferably, R1 is alkyl-phenyl group, more preferably methylphenyl group, more preferably p-methylphenyl group.

Preferably, in formula (I), R2 and R3 are independently chosen from the group consisting of hydrogen and alkyl groups comprising 1-20 carbon atoms, more preferably alkyl groups comprising 1-5 carbon atoms, more preferably ethyl group.

Alternatively, in formula (I), R2 and R3 form a ring together with the nitrogen atom attached to the phosphorous atom, wherein the ring is a five or six membered ring. Examples of a six membered ring include piperidyl, piperaziny and morpholine. Preferably, the ring is a five membered ring, most preferably pyrrolydinyl.

In some particularly preferred embodiments, in formula (I), R1 is p-methylphenyl and R2 and R3 are both ethyl, i.e. the compound (I) is represented by formula (II)

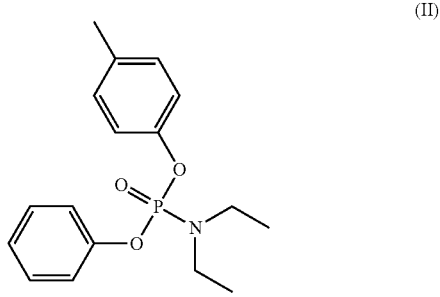 [SMILES: CCN(CC)P(=O)(Oc1ccccc1)Oc1ccc(C)cc1]

(II)

In some particularly preferred embodiments, in formula (I), R1 is p-methylphenyl and R2 and R3 form pyrrolidinyl group together with the nitrogen atom attached to the phosphorous atom, i.e. the compound (I) is represented by formula (III)

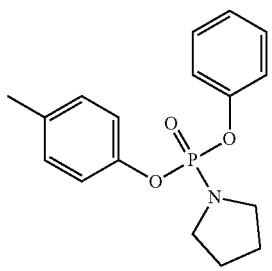

(III)

The compounds of formula (II) and (III) thermally degrade between 200 and 300° C., similar to the results of halogen containing flame retardants for EPS.

According to another aspect, the present invention relates to the compound according to formula (II) or (III).

The present invention further relates to the use of the compound according to formula (II) or (III) as a flame retardant. The present invention further relates to the use of the compound according to formula (II) or (III) as a flame retardant for a polymer composition. The present invention further relates to the use of the compound according to formula (II) or (III) as a flame retardant for a polymer composition comprising styrene. The present invention further relates to the use of the compound according to formula (II) or (III) as a flame retardant for a polymer composition comprising styrene, wherein the polymer composition is an expandable polymer composition.

The compound of formula (II) or (III) may be prepared by a process comprising the steps of:
(i) reacting phenyl dichlorophosphate and p-cresol in the presence of triethylamine and
(ii) reacting diethylamine and the reaction product of step (i) to obtain the compound of formula (II) or reacting pyrrolidine and the reaction product of step (i) to obtain the compound of formula (III).

Step (i) may for example be performed by adding a tetrahydrofuran solution of p-cresol and triethylamine to a tetrahydrofuran solution of phenyl dichlorophosphate and stirring the mixture solution. The solution of phenyl dichlorophosphate may be cooled before the addition of the solution of p-cresol and triethylamine. The stirring may e.g. be for 12-24 hours and at room temperature.

Step (ii) may for example be performed by adding diethylamine or pyrrolidine dropwise to the reaction product of step (i) and stirring. The stirring may e.g. be for 4-12 hours and at room temperature.

It is noted that US2004/0249029 describes a flame-retardant processing agent for polyester-based fiber products represented by a diaryl aminophosphate represented by formula:

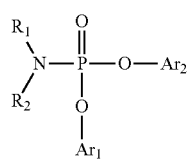

wherein Ar1 and Ar2 independently denote an aryl group, R1 and R2 independently denote a hydrogen atom, a lower alkyl group, a cycloalkyl group, an aryl group, an allyl group or an aralkyl group, or R1 and R2 may be combined together to form a ring. US2004/0249029 does not describe the use of the flame-retardant processing agent for polystyrene or EPS.

It is further noted that U.S. Pat. No. 3,937,765 describes a method for preparing O,O-diaryl N,N-dialkyl phosphoramidates for use as a flame retardant in a polyurethane foam. U.S. Pat. No. 3,937,765 does not describe the use of the flame-retardant processing agent for polystyrene or EPS.

It is further noted that JP2000-154277 discloses a flame-retarding resin composition containing phorporic acid amides such as diphenyl (cyclohexylamido) phosphate. JP2000-154277 does not disclose the compound of formula (III).

EPS

The polystyrene composition comprising the compound of formula (I) is preferably an expandable polystyrene (EPS) composition.

The EPS composition may be produced by a method comprising, in a first step, forming a fire retardant mixture comprising the compound (I) and polystyrene by intimately mixing in melt; and in a second step, forming the EPS composition by intimately mixing in melt the fire retardant mixture with a blowing agent.

Preferably the first step is performed in a first extruder and the second step is performed in a tandem extruder comprising extruder A and extruder B. Intimate mixing of the fire retardant mixture and blowing agent to form the EPS composition occurs in extruder A of the tandem extruder and cooling of the EPS composition occurs in extruder B of the tandem extruder. Cooling of the EPS composition prevents premature foaming of the blend at the die.

Blowing Agent

In general, useful blowing agents are volatile liquids and include but are not limited to aliphatic hydrocarbons, straight chain or branched, with up to 10 carbons; ketones such as acetone and methylethylketone; short chain alcohols such as alcohols having up to 10 carbons; and cycloaliphatic hydrocarbons. Preferred blowing agents are all pentane isomers and mixtures of pentane isomers. An especially preferred blowing agent is n-pentane. Blowing agents are typically used in amounts of about 2 wt % to about 20 wt % based on the weight of the composition, with about 2 wt % to about 10 wt % preferred based on the weight of the composition.

PPE Resin

The EPS composition may further comprise a polyphenylene ether (PPE) resin. Examples of the PPE resin are mentioned in WO2013/034276. The PPE resin is normally a homo- or copolymer having units of the formula

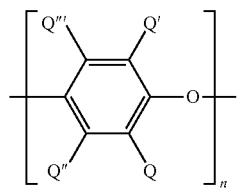

wherein Q, Q', Q", a'" are independently selected from the group consisting of hydrogen, halogen, hydrocarbon, halohydrocarbon, hydrocarbonoxy and halohydrocarbonoxy; and n represents the total number of monomer units and is an integer of at least about 20, and more usually at least 50.

The polyphenylene ether resin can be prepared in accordance with known procedures, such as those described in Hay, U.S. Pat. Nos. 3,306,874 and 3,306,875; and Stamatoff, U.S. Pat. Nos. 3,257,357 and 3,257,358; from the reaction of phenols including but not limited to 2,6-dimethylphenol; 2,6-diethylphenol; 2,6-dibutylphenol; 2,6-dilaurylphenol; 2,6-dipropylphenol; 2,6-diphenylphenol; 2-methyl-6-tolylphenol; 2-methyl-6-methoxyphenol; 2,3,6-trimethylphenol; 2,3,5,6-tetramethylphenol; and 2,6-diethyoxyphenol.

Each of these may be reacted alone to produce the corresponding homopolymer, or in pairs or with still other phenols to produce the corresponding copolymer. Examples of the homopolymer include poly(2,6-dimethyl-1, 4-phenylene)ether, poly(2,6-diethyl-1,4-phenylene)ether, poly(2,6-dibutyl-1,4-phenylene)ether, poly(2,6-dilauryl-1, 4-phenylene)ether, poly(2,6-dipropyl-1,4-phenylene)ether, poly(2,6-diphenyl-1,4-phenylene)ether, poly(2-methyl-6-methoxy-1,4-phenylene)ether, poly(2-methyl-6-butyl-1,4-phenylene)ether, poly(2,6-dimethoxy-1,4-phenylene)ether, poly(2,3,6-trimethyl-1,4-phenylene)ether, poly(2,3,5,6-tetramethyl-1,4-phenylene)ether, and poly(2,6-diethyoxy-1,4-phenylene)ether. Examples of the copolymer include, especially those of 2,6-dimethylphenol with other phenols, poly(2,6-dimethyl-co-2,3,6-trimethyl-1,4-phenylene)ether and poly(2,6-methyl-co-2-methyl-6-butyl-1,4-phenylene)ether.

For the purposes of the present invention, an especially preferred family of polyphenylene ethers includes those having alkyl substitution in the two positions ortho to the oxygen ether atom, i.e. those of the above formula wherein Q and Q' are alkyl, most preferably having 1 to 4 carbon atoms. Illustrative members of this class are: poly(2,6-dimethyl-1,4-phenylene)ether; poly(2,6-diethyl-1,4-phenylene)ether; poly(2-methyl-6-ethyl-1,4-phenylene)ether; poly(2-methyl-6-propyl-1,4-phenylene)ether; poly(2,6-dipropyl-1,4-phenylene)ether; poly(2-ethyl-6-propyl-1,4-phenylene) ether; and the like.

The most preferred polyphenylene ether resin for purposes of the present invention is poly(2,6-dimethyl-1,4-phenylene)ether.

The polyphenylene ether resin may be present in about 5 weight percent (wt %) to 95 wt % based on the weight of the composition, preferably about 30 wt % to about 60 wt % based on the weight of the composition.

In some embodiments, the composition according to the present invention comprises no or little amount, e.g. less than 0.01 wt % of a polyphenylene ether resin. This is preferable in view of the ease of recycle of the EPS beads.

Impact Modifier

The EPS composition may further comprise an impact modifier. Particularly suitable impact modifiers are the so called block copolymers, for example, A-B-A triblock copolymers and A-B diblock copolymers.

The A-B and A-B-A type block copolymer rubber additives which may be used are thermoplastic rubbers comprised of one or two alkenyl aromatic blocks which are typically styrene blocks and a rubber block, e. g., a butadiene block which may be partially hydrogenated. Mixtures of these triblock copolymers and diblock copolymers are especially useful. All impact modifiers generally used for compositions comprising a poly (arylene ether) resin, a polystyrene or a combination of a poly (arylene ether) resin and a polystyrene can be used.

Suitable A-B and A-B-A type block copolymers are disclosed in, for example, U.S. Pat. Nos. 3,078,254, 3,402, 159, 3,297,793, 3,265,765, and 3,594,452 and U. K. Patent 1,264,741. Examples of typical species of A-B and A-B-A block copolymers include polystyrene-polybutadiene (SBR), polystyrene-poly (ethylenepropylene), polystyrene-polyisoprene, poly (a-methylstyrene)-polybutadiene, poly-styrene-polybutadiene-polystyrene (SBS), polystyrene-poly (ethylene-propylene)polystyrene, polystyrene-polyisoprene-polystyrene and poly (a-methylstyrene)-polybutadiene-poly (a-methylstyrene), as well as the hydrogenated versions thereof, and the like. Mixtures comprising at least one of the aforementioned block copolymers are also useful. Such A-B and A-B-A block copolymers are available commercially from a number of sources, including Philips Petroleum under the trademark SOLPRENE, Shell Chemical Co., under the trademark KRATON, Dexco under the tradename VECTOR, and Kuraray under the trademark SEPTON.

A useful amount of impact modifier is up to about 30 wt % based on the weight of the composition, with about 5 wt % to about 15 wt % based on the weight of the composition preferred. In an especially preferred embodiment, the impact modifier comprises a polystyrene-polybutadiene-polystyrene block copolymer.

Non-halogenated, fire retardant, expandable poly (arylene ether)/polystyrene blends can also include effective amounts of at least one additive selected. Possible additives include anti-oxidants; drip retardants; coating additives; dyes; pigments; colorants; nucleating agents; stabilizers; small particle minerals such as clay, mica, and talc; antistatic agents; plasticizers, lubricants; mold release agents; and mixtures comprising at least one of the foregoing additives. Effective amounts of the additives vary widely, but they are usually present in an amount up to about 50% or more by weight, based on the weight of the entire composition.

Water as Blowing Agent

To improve foamability, finely dispersed droplets of internal water may be introduced into the styrene polymer matrix. An example of a method for this is the addition of water to the molten styrene polymer matrix. The location of addition of the water may be upstream of, together with, or downstream of, the blowing agent feed. Dynamic or static mixers can be used to achieve homogeneous distribution of the water. An adequate amount is generally from 0 to 2% by weight of water, preferably from 0.05 to 1.5% by weight, based on the styrene polymer.

Expandable styrene polymers (EPS) with at least 90% of the internal water in the form of droplets of internal water with diameter in the range from 0.5 to 15 pm form, on foaming, foams with an adequate number of cells and with homogeneous foam structure.

The amount added of blowing agent and of water is selected in such a way that the expansion capability of the expandable styrene polymers (EPS), defined as bulk density prior to foaming/bulk density after foaming, is at most 125, preferably from 25 to 100.

Suspension Polymerization

It is also possible to produce the expandable styrene polymers (EPS) of the invention via suspension polymerization.

In the suspension polymerization process, it is preferable to use styrene alone as monomer. However, up to 20% of its weight can have been replaced by other ethylenically unsaturated monomers, such as alkylstyrenes, divinylbenzene, acrylonitrile, 1,1-diphenyl ether or alpha-methylstyrene.

The usual auxiliaries can be added during the suspension polymerization process, examples being peroxide initiators, suspension stabilizers, blowing agents, chain-transfer agents, expansion aids, nucleating agents, and plasticizers. The amounts of the compound (I) added in the polymerization process are from 0.5 to 25% by weight, preferably from 5 to 15% by weight. The amounts of blowing agents added are from 3 to 10% by weight, based on monomer. These amounts can be added prior to, during, or after polymerization of the suspension. Suitable blowing agents are aliphatic hydrocarbons having from 4 to 6 carbon atoms. It is advantageous to use inorganic Pickering dispersants as suspension stabilizers, an example being magnesium pyrophosphate or calcium phosphate.

The suspension polymerization process produces bead-shaped particles which are in essence round, with average diameter in the range from 0.2 to 2 mm.

Final Steps

In order to improve processability, the finished expandable styrene polymer pellets can be coated with glycerol ester, antistatic agent, or anticaking agent.

The EPS pellets can be coated with glycerol monostearate GMS (typically 0.25%), glycerol tristearate (typically 0.25%), Aerosil R972 fine-particle silica (typically 0.12%), or Zn stearate (typically 0.15%), or else antistatic agent.

Foaming

The expandable styrene polymer pellets of the invention can be prefoamed in a first step by means of hot air or steam to give foam beads with density in the range from 8 to 200 kg/m$^3$, in particular from 10 to 50 kg/m$^3$, and can be fused in a second step in a closed mold, to give molded foams.

The expandable polystyrene particles can be processed to give polystyrene foams with densities of from 8 to 200 kg/m$^3$, preferably from 10 to 50 kg/m$^3$. To this end, the expandable beads are prefoamed. This is mostly achieved by heating of the beads, using steam in what are known as prefoamers. The resultant prefoamed beads are then fused to give moldings. To this end, the prefoamed beads are introduced into molds which do not have a gas-tight seal, and are treated with steam. The moldings can be removed after cooling.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention is now elucidated by way of the following examples, without however being limited thereto.

EXAMPLES

Phosphate amine esters were synthesized from phenyl-dichlorophosphate by the replacement of one of the chlorines by a substituted alcohol and the other chlorine by a secondary amine, see FIG. 1 showing the reaction scheme for the preparation of the phosphate amine esters.

Example 1

Preparation of diethyl[(4-methylphenoxy)(phenoxy)phosphoryl]amine (formula (II))

Phenyl dichlorophosphate (5 g, 23.7 mmol) was dissolved in THF (100 ml) and was cooled in an ice-bath to <10° C. Triethylamine (4.8 g, 47.4 mmol) and p-cresol (2.55 g 23.6 mmol) was added and the solution was stirred for 2 hours at room temperature. Diethylamine (1.72 g, 23.6 mmol) was added drop-wise and the reaction mixture was stirred overnight at room temperature. Water (50 ml) and ethyl acetate (100 ml) was added and the phases were separated. The organic phase was washed with water, filtered through a plug of silica and evaporated to yield 4.6 g product as oil.

$^1$H NMR (CDCl$_3$, ppm) δδ7.05-7.40 (9H, m, aromatic protons), δδ3.35 (4H, m, CH2CH3), δδ2.3 (3H, s, OCH3), δδ1.76 (6H, m, CH2CH3). $^{13}$C NMR (CDCl$_3$, ppm) δδ151 (1C) δ 149 (1C), δ 134 (1C) δδ130 (2C), δδ129 (2C), δδ124 (1C), δ 120 (2C), δ 119 (2C), δ 39 (2C), δ 21 (s, 1C), δδ14 (s, 2C).

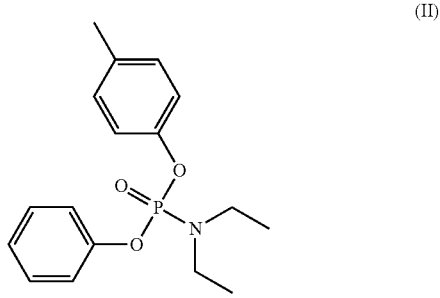 [SMILES: CCN(CC)P(=O)(Oc1ccccc1)Oc1ccc(C)cc1]

(II)

Example 2

Preparation of 4-methylphenyl phenyl pyrrolidin-1-ylphosphonate (formula (III))

Phenyl dichlorophosphate (5 g, 23.7 mmol) was dissolved in THF (100 ml) and was cooled in an ice-bath to <10° C. Triethylamine (4.8 g, 47.4 mmol) and p-cresol (2.55 g 23.6 mmol) was added and the solution was stirred for 2 hours at room temperature. Pyrrolidine (1.68 g, 23.6 mmol) was added drop-wise and the reaction mixture was stirred overnight at room temperature. Water (50 ml) and ethyl acetate (100 ml) was added and the phases were separated. The organic phase was washed with water, filtered through a plug of silica and evaporated to yield 7 g product as oil.

$^1$H NMR (CDCl$_3$, ppm) δδ7.05-7.35 (9H, m, aromatic protons), δδ3.25 (4H, t, CH2CH3), δδ2.35 (3H, s, OCH3), δδ1.05 (6H, m, CH2CH3). $^{13}$C NMR (CDCl$_3$, ppm) δδ152 (1C) δδ148 (1C), δδ134 (1C) δδ130 (2C), δδ129 (2C), δδ125 (1C), δδ120 (2C), δδ119 (2C), δδ47 (2C), δδ27 (2C), δδ21 (1C).

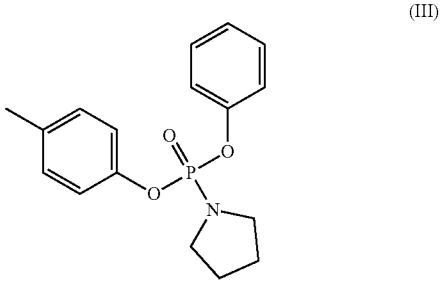 [SMILES: Cc1ccc(OP(=O)(Oc2ccccc2)N2CCCC2)cc1]

(III)

The invention claimed is:

1. A polystyrene composition comprising polystyrene and a compound according to formula (III),

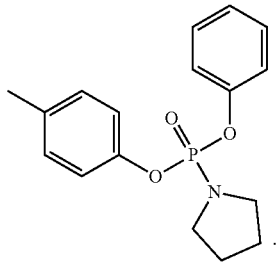

2. The polystyrene composition according to claim 1, wherein the amount of the compound (III) is 1-10 wt % of the total composition.

3. The polystyrene composition according to claim 1, wherein the polystyrene composition is an expandable polystyrene composition.

4. A compound according to Formula (III),

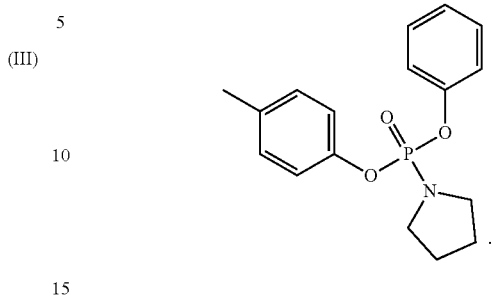

5. A process for the preparation of the compound according to claim 4, comprising:
   (i) reacting phenyl dichlorophosphate and p-cresol in the presence of triethylamine and
   (ii) reacting pyrrolidine and the reaction product of step (i) to obtain the compound of formula (III).

6. The polystyrene composition of claim 1, further comprising a polyphenylene ether resin.

* * * * *